United States Patent [19]

Poss

[11] Patent Number: 5,208,235
[45] Date of Patent: May 4, 1993

[54] INDOLE- AND BENZIMIDAZOLE-SUBSTITUTED IMIDAZOLE DERIVATIVES

[75] Inventor: Michael A. Poss, Lawrenceville, N.J.

[73] Assignee: E. R. Squibb & Sons, Inc., Princeton, N.J.

[21] Appl. No.: 849,118

[22] Filed: Mar. 10, 1992

[51] Int. Cl.$^5$ .............. A61K 31/535; A61K 31/445; C07D 413/14; C07F 9/28
[52] U.S. Cl. .................. 514/235.8; 514/255; 514/326; 514/374; 514/385; 514/386; 514/387; 514/397; 544/139; 544/337; 546/22; 548/111; 548/112; 548/113
[58] Field of Search .................. 548/111, 112, 113; 546/22; 544/139, 337; 514/374, 326, 235.8, 255, 385, 386, 387, 397

[56] References Cited

U.S. PATENT DOCUMENTS 4,335,040 10/1982 Furukawa et al. .................. 424/273

FOREIGN PATENT DOCUMENTS 253310 1/1988 European Pat. Off. ............ 548/337
400974 12/1990 European Pat. Off. ............ 548/342
429257 5/1991 European Pat. Off. ............ 548/337

OTHER PUBLICATIONS

CA 115(17):183302K Preparation of ... inhibitors, Ross et al., p. 928, 1991.

*Primary Examiner*—Mary C. Lee
*Assistant Examiner*—Joseph K. McKane
*Attorney, Agent, or Firm*—Ellen K. Park

[57] ABSTRACT

Novel compounds having the formula

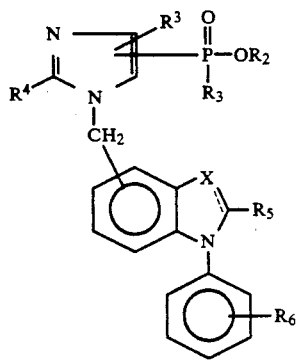

where X $R_1$, $R_2$, $R_3$, $R_4$, $R_5$ and $R_6$ are as defined herein. These compounds inhibit the action of angiotensin II and are useful, therefore for example, as antihypertensive agents.

19 Claims, No Drawings

INDOLE- AND BENZIMIDAZOLE-SUBSTITUTED IMIDAZOLE DERIVATIVES

FIELD OF THE INVENTION

The present invention relates to novel substituted imidazoles which are useful as antihypertensive agents.

SUMMARY OF THE INVENTION

In accordance with the present invention, novel compounds which inhibit the action of the hormone angiotensin II are disclosed. These compounds are of the general formula

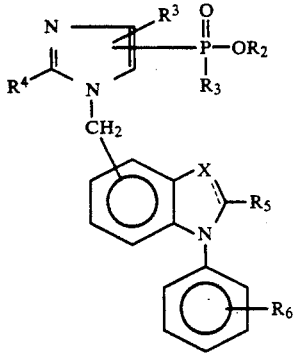

and pharmaceutically acceptable salts and prodrugs thereof.

As used in formula I, and throughout the specification, the symbols have the following meanings:

X is —N— or

the broken line adjacent to the X atom represents the optional presence of a double bond, provided that if X is nitrogen, the double bond must be present;

$R_1$ is hydrogen, halogen, —CF$_3$ or —CF$_2$CF$_3$;

$R_2$ is hydrogen or $R_7$;

$R_3$ is hydroxy or $R_8$;

$R_4$ is alkyl, alkenyl or alkynyl or an alkyl, alkenyl or alkynyl group substituted with one or more F or —CO$_2$R$_9$ groups; cycloalkyl; (cycloalkyl)alkyl of 4 to 10 carbon atoms; (cycloalkyl)alkenyl or (cycloalkyl)alkynyl of 5 to 10 carbon atoms; —NR$_{12}$R$_{13}$; —(CH$_2$)$_n$Z(CH$_2$)$_p$R$_{15}$; benzyl or benzyl substituted with 1 or 2 halogens, alkoxy of 1 to 4 carbon atoms, alkyl of 1 to 4 carbon atoms, haloalkyl or nitro; —SR$_{16}$ or —OR$_{16}$;

$R_5$ and $R_5'$ are independently selected from hydrogen, alkyl, aryl, cycloalkyl, arylalkyl, haloalkyl, —CO$_2$R$_9$, —NHSO$_2$CF$_3$, —OS(O)(OH)$_2$, —SO$_3$H,

—C(CF$_3$)$_2$OH, —OP(O)(OH)$_2$, —PO$_3$H$_2$, —NHP(O)(OH)$_2$,

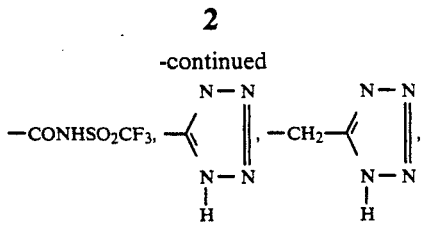

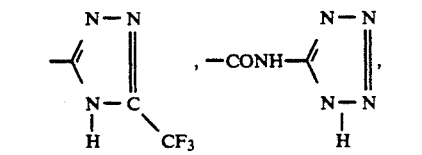

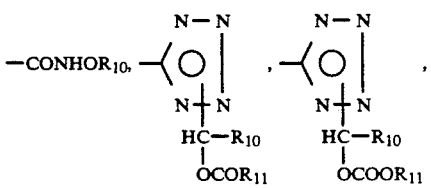

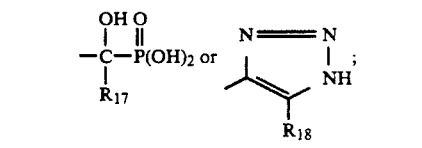

$R_6$ is an acid moiety such as hydrogen,

—CO$_2$R$_9$, —NHSO$_2$CF$_3$, —OS(O)(OH)$_2$, —SO$_3$H, —C(CF$_3$)$_2$OH,

—OP(O)(OH)$_2$, —PO$_3$H$_2$, —NHP(O)(OH)$_2$, —CONHSO$_2$CF$_3$,

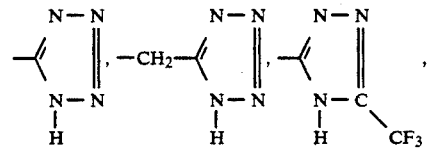

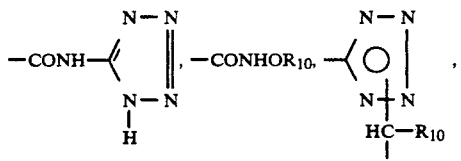

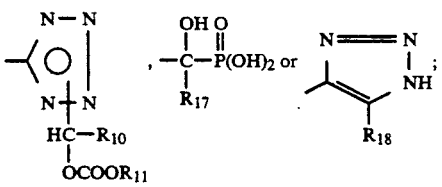

$R_7$ is alkyl of 1 to 6 carbon atoms, cycloalkyl of 3 to 6 carbon atoms, arylalkyl, alkylaryl or phenyl;

$R_8$ is alkyl of 1 to 6 carbon atoms, alkylaryl, cycloalkyl of 3 to 6 carbon atoms or OR$_7$;

$R_9$ is hydrogen, alkyl, perfluoroalkyl of 1 to 8 carbon atoms, cycloalkyl of 3 to 6 carbon atoms, phenyl, benzyl,

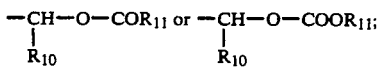

$R_{10}$ is hydrogen, alkyl, aryl, alkylaryl, arylalkyl or cycloalkyl;

$R_{11}$ is alkyl, aryl, alkylaryl, arylalkyl or cycloalkyl;

$R_{12}$ and $R_{13}$ are independently hydrogen, alkyl of 1 to 6 carbon atoms, benzyl, α-methylbenzyl, or taken together with the nitrogen atom to which they are attached form a ring of the formula

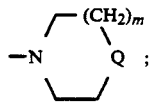

$R_{14}$ is hydrogen, alkyl of 1 to 6 carbon atoms, cycloalkyl of 3 to 6 carbon atoms, phenyl or benzyl;

$R_{15}$ is hydrogen; alkyl of 1 to 6 carbon atoms; cycloalkyl; alkenyl or alkynyl of 2 to 4 carbon atoms; or the above alkyl, cycloalkyl, alkenyl or alkynyl group optionally-substituted with F or $-CO_2R_9$;

$R_{16}$ is alkyl, alkenyl, alkynyl, aryl, arylalkyl, cycloalkyl, (cycloalkyl)alkyl, heterocyclo, (heterocyclo)alkyl or haloalkyl;

$R_{17}$ is hydrogen, alkyl of 1 to 5 carbon atoms or phenyl;

$R_{18}$ is $-CN$, $-NO_2$ or $-CO_2R_9$;

Q is $-CH_2$, $-O-$, or $-NR_{10}$;

Z is $-O-$, $-S-$ or $-NR_{14}$;

m is 0, or the integer 1;

n is an integer of 1 to 5; and p is an integer of 1 to 5.

DETAILED DESCRIPTION OF THE INVENTION

The present invention relates to the compounds of formula I (and pharmaceutically acceptable salts and prodrugs thereof), pharmaceutical compositions employing such compounds and to methods of using such compounds. Listed below are definitions of various terms used to describe the compounds of the instant invention. These definitions apply to the terms as they are used throughout the specification (unless they are otherwise limited in specific instances) either individually or as part of a larger group.

The term "alkyl" refers to both straight and branched chain groups having 1 to 10 carbon atoms. Alkyl groups having 1 to 4 carbon atoms are preferred.

The terms "alkenyl" and "alkynyl" refer to both straight and branched chain groups. Those groups having 2 to 10 carbon atoms are preferred.

The term "cycloalkyl" refers to groups having 3 to 8 carbon atoms.

The term "alkoxy" refers to groups having 1 to 8 carbon atoms. Alkoxy groups having 1 to 3 carbon atoms are preferred.

The term "halogen" refers to fluorine, chlorine, bromine and iodine with fluorine and chlorine being preferred.

The term "haloalkyl" refers to such alkyl groups described above in which one or more hydrogens have been replaced by chloro, bromo or fluoro groups such as trifluoromethyl, pentafluoroethyl, 2,2,2-trichloroethyl, chloromethyl, bromomethyl, etc., trifluoromethyl being preferred.

The term "aryl" refers to phenyl or naphthyl or phenyl or naphthyl substituted with substituents selected from halogen, alkyl, alkoxy, carboxy, alkylthio, hydroxy, alkanoyl, nitro, amino, alkylamino, dialkylamino or trifluoromethyl groups. Preferred aryl groups are phenyl and monosubstituted phenyl and phenyl is most preferred.

The term "heterocyclo" refers to fully saturated or unsaturated rings of 5 or 6 atoms containing one to four nitrogen atoms, or one oxygen atom, or one sulfur atom, or one oxygen atom and one or two nitrogen atoms, or one sulfur atom and one or two nitrogen atoms. Preferred monocyclic heterocyclo groups include 2- and 3-thienyl, 2- and 3-furyl, 2-, 3- and 4-pyridyl, and imidazolyl. The heterocycle may also have a substituent selected from alkyl of 1 to 4 carbons, carboxy, alkoxy of 1 to 4 carbons and alkylthio of 1 to 4 carbons on an available carbon. The term heterocyclo also includes bicyclic rings wherein the five or six membered ring containing oxygen, sulfur and nitrogen atoms as defined above is fused to a benzene ring and the bicyclic ring is attached by way of an available carbon atom in the benzene ring. Preferred bicyclic heterocyclo groups include 4, 5, 6 or 7-indolyl, 4, 5, 6 or 7-isoindolyl, 5, 6, 7 or 8-quinolinyl, 5, 6, 7 or 8-isoquinolinyl, 4, 5, 6, or 7-benzothiazolyl, 4, 5, 6 or 7-benzoxazolyl, 4, 5, 6 or 7-benzimidazolyl, 4, 5, 6 or 7-benzoxadiazolyl, and 4, 5, 6 or 7-benzofuranyl. Preferred fused heterocycles include thienyl, furyl, pyridyl and imidazolyl, optionally substituted as described above.

All stereoisomers of the compounds of the instant invention are contemplated, either in admixture or in pure or substantially pure form.

It should be understood that the present invention includes prodrug forms, such as ester, acetal and/or mixed acetal derivatives of the compounds of formula I. For example, such derivatives have been documented in *Design of Prodrugs*, edited by H. Bundgard, (Elsevier, 1985) and *Methods in Enzymology*, Vol. 42, p. 309-396, edited by K. Widder et al. (Academic Press, 1985). Further, it is understood that any moiety at $R_2$, $R_3$, $R_5$ and/or $R_6$ that will be cleaved in vivo to provide an acidic $R_2$, $R_3$, $R_5$ and/or $R_6$ moiety is within the spirit and scope of this invention.

An exemplary process for preparing the compounds of formula I where $R_2$ is $R_7$ and $R_3$ is $R_8$, includes coupling a compound of the formula

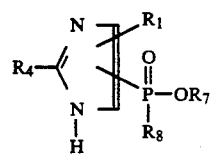

II with a compound of the formula

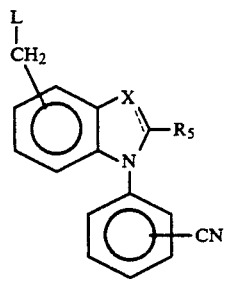

wherein L is a leaving group such as a halogen, in the presence of a coupling agent such as cesium carbonate in an organic solvent such as tetrahydrofuran or dimethylformamide, to provide the compound

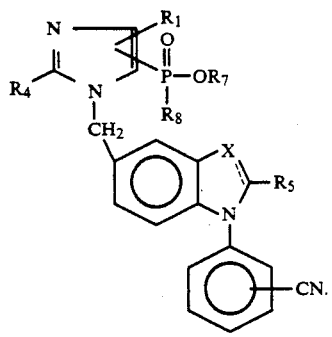

Compounds of formula IV can thereafter be treated with an azide such as tributyltin azide in an organic solvent such as xylene to provide the formula I compounds where $R_2$ is $R_7$ and $R_3$ is $R_8$. Subsequent de-esterification by treatment with a base such as potassium hydroxide or a Lewis acid such as trimethylsilylbromide, provides the other compounds of formula I, (i.e. where $R_2$ is hydrogen and $R_3$ is hydroxy).

Compounds of formula II may also be coupled with compounds of formula

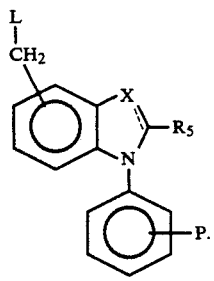

where P is a protected $R_6$ acid moiety such as

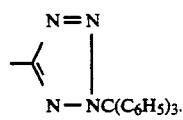

to form compounds of formula

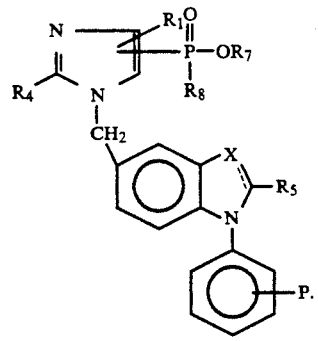

Compounds of formula IVa are then deprotected with a strong acid such as hydrochloric acid in an organic solvent such as tetrahydrofuran to provide compounds of formula I where $R_2$ is $R_7$ and $R_3$ is $R_8$. Subsequent treatment as described previously provides the other formula I compounds (i.e. where $R_2$ is hydrogen and $R_3$ is hydroxy).

The imidazole Ii can be prepared by reacting imidazole with an orthoester such as triethyl ortho formate in the presence of an acid such as para-toluenesulfonic acid to form a compound of formula

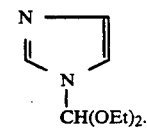

Compounds of formula V are then reacted with a strong base such as n-butyllithium and an alkyl halide such as n-butyliodide ($R_4$=n-Bu) in an organic solvent such as tetrahydrofuran to form compounds of formula

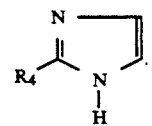

Compounds of formula VI are then halogenated with bromine (hal=Br) or NCS (hal=Cl) in an organic solvent such as chloroform to form compounds of formula

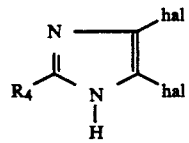

Compounds of formula VII are then reacted with a protecting group such as 2-(trimethylsilyl)-ethoxymethyl chloride and a base such as sodium hydride in an organic solvent such as tetrahydrofuran to form compounds of formula

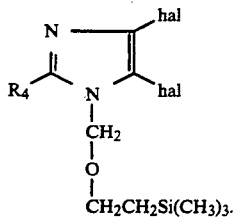  VIII

Compounds of formula VIII may then be reacted with a strong base such as n-butyllithium and a compound of formula hal—PO(OR$_7$)R$_8$ such as diethylchlorophosphate in an organic solvent such as tetrahydrofuran to form

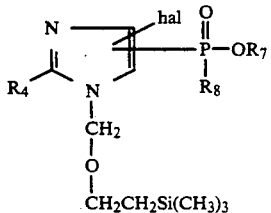  IX where R$_8$ is OR$_7$. To form compounds of formula IX where R$_8$ is other than OR$_7$, compounds of formula VIII are reacted with a compound of formula ClP(OR$_7$)$_2$ to form compounds of formula

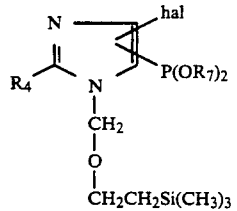  IXa which is then treated with, for example, an alkyl halide such as methyl iodide (R$_8$=methyl) to form the compounds of formula IX, where R$_8$ is other than OR$_7$.

Treatment of formula IX compounds with an acid such as hydrochloric acid in an organic solvent such as tetrahydrofuran, to remove the protecting group provides the formula II compounds where R$_1$ is halogen. To obtain compounds of formula II where R$_1$ is hydrogen, compounds of formula IX are first reacted with hydrogen, in the presence of a catalyst such as Pd/(OH)$_2$, in an organic solvent such as ethanol, prior to deprotection with the acid. Compounds of formula II where R$_1$ is —CF$_3$ or —CF$_2$CF$_3$ may be prepared by methods similar to those described above using, for example, 4-trifluoromethyl imidazole (J. J. Baldwin et at., *J. Med. Chem.*, 18, 895, 1975).

Compounds of formula III where X is

can be prepared by coupling a compound of the formula

  X with a compound of the formula

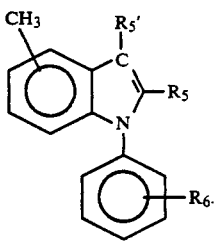  XI where X is bromide in a polar solvent such as pyridine and in the presence of a catalyst such as copper oxide, to provide compounds of the formula

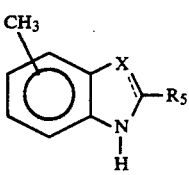  XII

A leaving group, L, for example a halogen can be added by known methodology to provide compounds of the formula

  IIIb

Compounds of formula X can be prepared by known techniques such as those described in *J. Heterocyclic Chem.*, 25, 1 (1988).

Compounds of formula III where X is

nitrogen may also be prepared by reacting a compound of the formula

XIII with a compound of the formula

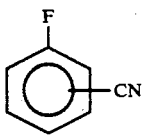  XIV in the presence of a base such as potassium carbonate, and in an organic solvent such as dimethylformamide, to provide a compound of the formula

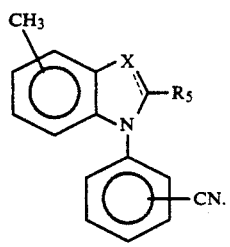  XV

Compound XV can thereafter be treated with a brominating agent such as N-bromosuccinimide and a radical initiator such as 2,2'-azobisisobutyronitrile, in an organic solvent such as carbon tetrachloride, to provide a compound of the formula

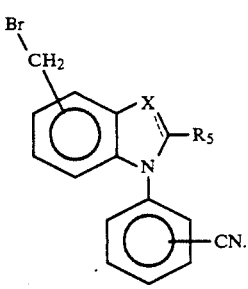  XVI

Intermediate XVI can be coupled with the compound of formula II to provide the formula IV compounds which can then be treated with an azide such as tributyltin azide to provide compounds of formula I, where $R_6$ is

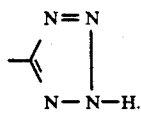

Compounds of formula I where $R_6$ is other than

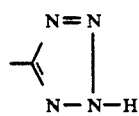

can be prepared by using intermediate XI (where X is fluorine) in place of compound XIV above.

Compounds of formula XIII where X is nitrogen are prepared as described by Mathias et al., *Synthetic Communications,* 5, 461–469 (1975).

Compounds of formula IIIa may be prepared by reacting a compound of formula

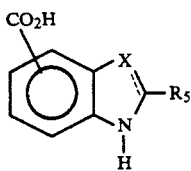  XVIII with an esterifying agent such as ethereal diazo methane to form compounds of formula

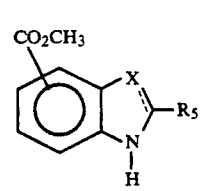  XIX

Compounds of formula XIX are then coupled with a compound of formula XIV in the presence of a base such as potassium carbonate and in an organic solvent such as dimethylformamide, to provide a compound of formula

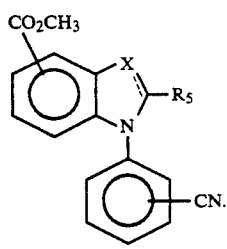  XX

Compound XX can thereafter be treated with an azide such as tributyltin azide and a protecting group such as triphenylmethyl chloride in the presence of a base such as triethylamine to form compounds of formula

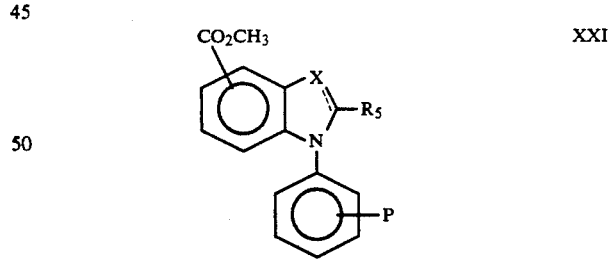  XXI where P is a protected $R_6$ acid moiety such as

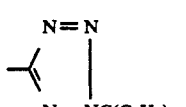

Compounds of formula XXI are then reacted with a reducing agent such as lithium aluminum hydride in an organic solvent such as tetrahydrofuran to form the alcohols of formula

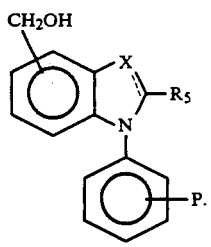

Compounds of formula XXII are then reacted with a brominating agent such as carbon tetrabromide/triphenyl phosphine to form the formula IIIa compounds.

Preferred compounds of the present invention are those wherein $R_1$ is hydrogen or halogen;
$R_2$ is hydrogen or an alkyl of 1 to 6 carbons;
$R_3$ is alkyl of 1 to 6 carbons, —OH or —O—alkyl of 1 to 6 carbon atoms;
$R_4$ is an alkyl of 2 to 10 carbons or alkenyl of 3 to 10 carbons;
$R_5$ is hydrogen or —$CO_2H$;
$R_6$ is ortho-tetrazolyl or —$CO_2H$; and
X is —N— or

where $R_5'$ is hydrogen or —$CO_2H$.

Most preferred are compounds of formula I wherein
$R_1$ is chlorine;
$R_2$ is ethyl or hydrogen;
$R_3$ is —OH;
$R_4$ is n-butyl;
$R_5$ is hydrogen;
$R_6$ is ortho-tetrazolyl;
X is

where $R_5'$ is hydrogen; and the imidazole nucleus is bonded to the 4-position of the indole.

The present compounds of formula I inhibit the action of the hormone angiotensin II (A-II) and are therefore useful, for example, as antihypertensive agents.

The action of the enzyme renin on angiotensinogen, a pseudoglobulin in blood plasma, produces angiotensin I. Angiotensin I is converted by angiotensin converting enzyme (ACE) to A-II. The latter is an active pressor substance which has been implicated as the causative agent in several forms of hypertension in various mammalian species, e.g., humans. The compounds of this invention inhibit the action of A-II at its receptors on target cells and thus prevent the increase in blood pressure produced by this hormone-receptor interaction. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg per kilogram of body weight per day, preferably about 1 to 15 mg per kilogram of body weight per day is appropriate to reduce blood pressure. The substance is preferably administered orally, but intranasal, transdermal and parenteral routes such as the subcutaneous, intramuscular, intravenous or intraperitoneal routes can also be employed. The compounds of this invention are also useful in the treatment of congestive heart failure and cardiac hypertrophy. In addition, in view of the role of these compounds in the renin-angiotensin system described above, the A-II antagonist compounds disclosed herein are also expected to be useful for the same or similar indications which have developed for ACE inhibitors.

The compounds of this invention can also be formulated in combination with a diuretic for the treatment of hypertension. A combination product comprising a compound of this invention and a diuretic can be administered in an effective amount which comprises a total daily dosage of about 30 to 600 mg, preferably about 30 to 330 mg of a compound of this invention, and about 15 to 300 mg, preferably about 15 to 200 mg of the diuretic, to a mammalian species in need thereof. Exemplary of the diuretics contemplated for use in combination with a compound of this invention are the thiazide diuretics, e.g., chlorthiazide, hydrochlorthiazide, flumethiazide, hydroflumethiazide, bendroflumethiazide, methylchlothiazide, trichlormethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, in sterile solutions or suspensions for parenteral or intranasal administration, or in transdermal patches. About 10 to 500 mg of a compound of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples and preparations describe the manner and process of making and using the invention and are illustrative rather than limiting. It should be understood that there may be other embodiments which fall within the spirit and scope of the invention as defined by the claims appended hereto.

EXAMPLE 1

[2-Butyl-1-[[1-[2-(2H-tetrazol-5-yl)phenyl]-1H-indol-4-yl]methyl]-1H-imidazol-4-yl]phosphonic acid, monoethyl ester, dipotassium salt A. 1-(Diethoxymethyl)-1H-imidazole Imidazole (6.81 g, 0.10 mol, 1.0 eq), triethyl orthoformate (66.5 mL, 0.40 mol, 4.0 eq) and para-toluenesulfonic acid (0.5 g) were combined and heated at 130° C. Ethanol was slowly distilled off. After the distillation of the ethanol ceased, the reaction was distilled using a floor pump (0.1 mm). Excess triethyl orthoformate distilled at 50° C. and then the product was distilled at 78°-84° C. to give the title compound (12.316 g, 72%).

B. 2-Butyl-1H-imidazole n-Butyl lithium (13.1 mL, 32.75 mmol, 1.05 eq, 2.5M in hexane) was added to a solution of the title A compound (5.309 g, 31.19 mmol, 1.0 eq) in tetrahydrofuran (78 mL, 0.4M) at −40° C. and stirred for 10 minutes. n-Butyl iodide (3.90 mL, 34.31 mmol, 1.1 eq) was then added. The ice bath was allowed to melt and the reaction was stirred at room temperature overnight. The mixture was diluted with ethyl ether (100 mL) and quenched with aqueous 1N hydrochloric acid till acidic. After the layers were separated, the organic phase was extracted three times with 0.1N hydrochloric acid. The combined aqueous washes were made basic with solid sodium bicarbonate and extracted four times with chloroform. The chloroform extracts were then dried over sodium sulfate, filtered through magnesium sulfate and concentrated to give the title compound (4.112 g, >100%). The crude product (3.0 g) was chromatographed on Merck silica gel (70 g) eluting with chloroform:methanol: ammonium hydroxide (30:1:0.5) followed by (30:1.5:0.05) followed by (30:3:0.05) to furnish the title compound (2.033 g, 70%).

C. 4,5-Dibromo-2-butyl-1H-imidazole

Bromine (0.97 mL, 18.74 mmol, 2.05 eq) in chloroform (18.3 mL, 0.5M) was added dropwise to a solution of the title B compound (1.135 g, 9.14 mmol, 1.0 eq) in chloroform (18.3 mL, 0.5M) at 0° C. After the addition was complete, the reaction was warmed to room temperature and stirred two hours. Saturated aqueous potassium carbonate and water were added till the solution was basic. The layers were separated and the aqueous was extracted twice with ethyl acetate. The combined organic extracts were dried over sodium sulfate, filtered through magnesium sulfate and concentrated. The residue was chromatographed on Merck silica gel (20 g) eluting with toluene:acetone:ammonium hydroxide (30:0.75:0.05) to furnish the title compound (1.034 g, 40%).

D. 4,5-Dibromo-2-butyl-1-[(phenylmethoxy)methyl]-1H-imidazole

Sodium hydride (319.5 mg, 6.65 mmol, 1.4 eq, 50% in oil) was added to a solution of the title C compound (1.3397 g, 4.75 mmol, 1.0 eq) in tetrahydrofuran (11.9 mL 0.4M) at 0° C. and stirred for 30 minutes. The reaction was then warmed to room temperature and stirred 30 minutes. Next, the mixture was cooled to 0° C. and benzyl chloromethyl ether (0.79 mL, 5.70 mmol, 1.2 eq) was added. The reaction was warmed to room temperature, stirred for 30 minutes and then quenched with aqueous saturated ammonium chloride and water. Next, the mixture was extracted three times with ethyl acetate. The organic extracts were dried over sodium sulfate, filtered through magnesium sulfate and concentrated. The residue was chromatographed on Merck silica gel (50 g) eluting with hexane: ether:triethyl amine (27:3:0.05) to give the title compound (1.617 g, 85%).

E. [4-Bromo-2-butyl-1-[(phenylmethoxy)methyl]-1H-imidazol-5-yl]-phosphonic acid, diethyl ester n-Butyl lithium (1.98 mL, 4.42 mmol, 1.1 eq, 2.23M in hexane) was added to a solution of the title D compound (1.617 g, 4.02 mmol, 1.0 eq) in tetrahydrofuran (16.1 mL, 0.25M) at −78° C. After five minutes, freshly distilled diethyl chlorophosphate (0.70 mL, 4.83 mmol, 1.2 eq) was added and the reaction was stirred for 10 minutes. The mixture was then warmed to room temperature, stirred for one hour, quenched with aqueous saturated ammonium chloride, and extracted three times with ethyl acetate. The organic extracts were dried over sodium sulfate, filtered through magnesium sulfate and concentrated. The residue was chromatographed on Merck silica gel (50 g) eluting with chloroform:ether:triethyl amine (30:1:0.05) followed by chloroform:ethyl acetate:triethyl amine (30:3:0.05) to provide the title compound (1.222 g, 66%).

F. (2-Butyl-1H-imidazol-5-yl)phosphonic acid, diethyl ester

The title E compound (1.187 g, 2.58 mmol, 1.0 eq) was combined with Pd(OH)$_2$ on carbon (237 mg, 20% by weight) in ethanol (12.9 mL, 0.2M) and placed under a balloon of hydrogen for two hours. More Pd(OH)$_2$ on carbon (100 mg) was then added and the reaction was stirred under an atmosphere of hydrogen overnight. The mixture was then diluted with methanol, filtered through regenerated cellulose and concentrated. The residue was pre-absorbed onto 5 g of silica and chromatographed on Merck silica gel (25 g) eluting with chloroform:methanol:ammonium hydroxide (30:1:0.05) to furnish the title compound (526 mg, 78%).

G. [2-Butyl-1-[[1-(2-cyanophenyl)-1H-indol-4-yl]methyl]-1H-imidazol-4-yl]phosphonic acid, diethyl ester

1. 1H-Indole-4-carboxylic acid, methyl ester

To a solution of indole-4-carboxylic acid (506 mg, 3.14 mmol) dissolved in a mixture of methanol (5 mL) and diethyl ether (10 mL) was added ethereal diazomethane until disappearance of the starting acid was indicated by TLC. Magnesium sulfate was then added and the solution filtered and concentrated in vacuo. Flash chromatography on Merck silica gel (10 g) eluted with 2:1, chloroform:hexanes, followed by 10:1, chloroform: ether afforded the title compound (540 mg, 98%).

2. 1-(2-Cyanophenyl)-1H-indole-4-carboxylic acid, methyl ester

A mixture of the title 1 compound (40.6 mg, 0.232 mmol), 2-fluorobenzonitrile (38 μL, 0.348 mmol), potassium carbonate (64.1 mg, 0.464 mmol), and 18-crown-6 (6.1 mg, 0.0232 mmol) in dimethylformamide (0.23 mL) was heated at 150° C. for 150 minutes. Upon cooling to room temperature, the reaction mixture was diluted with ethyl acetate, filtered and rinsed with pH 4 buffer. The aqueous layer was further extracted with two more portions of ethyl acetate and the combined organic extract was rinsed with brine, dried over sodium sulfate, filtered over sodium sulfate, and concentrated in vacuo. Flash chromatography on Merck silica gel (5 g) eluted with 5:1, chloroform:hexanes, followed by 100% chloroform afforded the title compound (61.6 mg, 96%).

3. 1-(2-Cyanophenyl)-1H-indole-4-carboxylic acid

The title 2 compound (8.0 g, 28.95 mmol), 1N sodium hydroxide (43.4 mL, 43.4 mmol), methanol (43.4 mL, 43.4 mmol) and tetrahydrofuran (43.4 mL) were combined and heated to 50° C. After four hours 40 minutes, the reaction was cooled to room temperature and 10% hydrochloric acid (∼50 mL) was added to precipitate a white solid. The mixture was filtered and the product was collected as a white solid (7.2 g, 95%).

4. 2-[4-(Hydroxymethyl)-1H-indol-4-yl]-benzonitrile

Borane-tetrahydrofuran complex (1M in tetrahydrofuran, 27.3 mL) was added to a solution of the title 3 compound (7.17 g, 27.3 mmol) in tetrahydrofuran (distilled, 27.3 mL) at −20° C., warmed to room temperature and stirred for 21 hours. The solution was cooled to 0° C. and quenched with 1N sodium hydroxide to pH=14. The solution was extracted with ether (3×100 mL), washed with sodium chloride, dried over magnesium sulfate, filtered and concentrated to a light green solid. The solid was recrystallized twice from ethyl acetate/hexane to yield the title compound (5.54 g, 82%).

5. 2-[4-(Bromomethyl)-1H-indol-1-yl]-benzonitrile

To a solution of the title 4 compound (5.46 g, 22 mmol) in methylene chloride (distilled, 60 mL) at 0° C. was added carbon tetrabromide (10.2 g, 30.8 mmol) and triphenylphosphine (7.5 g, 28.6 mmol). The reaction was stirred for 15 minutes at 0° C. and was then warmed to room temperature. After 2.5 hours, the reaction was diluted in methylene chloride and placed directly on a Merck silica gel column (66 g) eluting with (1:1) toluene/hexane for purification. The product fractions were collected and concentrated, then triturated with cold ethyl acetate to obtain the title compound (5.8 g, 85%).

6.
[2-Butyl-1-[[1-(2-cyanophenyl)-1H-indol-4-yl]methyl]-1H-imidazol-4-yl]phosphonic acid, diethyl ester The title F compound (474 mg, 1.82 mmol, 1.0 eq) was combined with the title 5 compound (595 mg, 1.91 mmol, 1.05 eq) and cesium carbonate (1.067 g, 3.28 mmol, 1.8 eq) in dimethylformamide (4.5 mL, 0.4M) at 0° C. The ice bath was allowed to melt and the reaction was stirred at room temperature overnight. The mixture was then diluted with ethyl acetate and filtered. The filtrate was combined with pH 4 buffer and extracted three times with ethyl acetate. The organic extracts were dried over sodium sulfate, filtered through magnesium sulfate, and concentrated. The residue was chromatographed on Merck silica gel (70 g) eluting with toluene: acetone:methanol:ammonium hydroxide (25:5:0.1:0.1) followed by (25:5:1:0.25) to give the title compound (535 mg, 60%).

H.
[2-Butyl-1-[[1-[2-(2H-tetrazol-5-yl)phenyl]-1H-indol-4-yl]methyl]-1H-imidazol-4-yl]-phosphonic acid, monoethyl ester The title G compound (321 mg, 0.655 mmol, 1.0 eq) was combined with tributyltinazide (1.305 g, 3.93 mmol, 6.0 eq) in xylene (1.3 mL, 0.5M) and heated at 110° C. for a total of 45 hours. The reaction was then cooled to room temperature and chromatographed on Merck silica gel (20 g) eluting with chloroform:methanol:ammonium hydroxide (30:0.8:0.05) followed by ethyl acetate:pyridine:acetic acid:water (16:2:2:1) to give the title compound (122.0 mg, 37%).

I.
[2-Butyl-1-[[1-(2H-tetrazol-5-yl)phenyl]-1H-indol-4-yl]methyl]-1H-imidazol-4-yl]-phosphonic acid, monoethyl ester, dipotassium salt The title H compound (122 mg, 0.241 mmol, 1.0 eq) was combined with potassium bicarbonate (60.3 mg, 0.602 mmol, 2.5 eq) in water at room temperature. After stirring, the mixture was filtered through a glass frit and chromatographed on an HP-20 column (15 mL) eluting with water followed by 20% acetone in water. The product fractions were concentrated to a small volume and lyophilized to give an intermediate (100 mg) which was then relyophilized to furnish the title compound (95 mg, 68%); m.p. 250°-253° C.

| Elemental Analysis (%) | | | |
|---|---|---|---|
| Cal'c: C 49,04; | H 4.84; | N 16.01; | P 5.06; |
| Found: C 49.02; | H 4.96; | N 15.72; | P 5.05. |

EXAMPLE 2

[4-Bromo-2-butyl-1-[[1-[2-(2H-tetrazol-5-yl)phenyl]-1H-indol-4-yl]methyl]-1H-imidazol-5-yl]phosphonic acid, monoethyl ester, dipotassium salt A. 1-(Diethoxymethyl)-1H-imidazole A mixture of imidazole (15 g, 0.220 mol, 1 eq), triethyl orthoformate (130 g, 146.6 mL, 0.880 mol, 4.0 eq) and p-toluenesulfonic acid (1.17 g, 0.00616 mol, 0.028 eq) was heated at 145°-175° C. until no more ethanol was distillable from the reaction mixture. The excess orthoformate was removed in vacuo, solid sodium bicarbonate (1.17 g, 0.011 mol) was added and the residue was vacuum distilled to give the title compound (23.6 g, 68 %). b.p. 89°-91° C./0.3 mm Hg.

B. 2-Butyl-1H-imidazole

To the title A compound (22.350 g, 142.181 mmol, 1 eq) in dry tetrahydrofuran (355 mL, 0.4 M) at −40° C. was added via syringe n-butyllithium (2.5M in hexane, 56.87 mL, 142.181 mmol, 1 eq) such that the temperature did not rise above −35° C. The mixture was stirred at −40° C. for 15 minutes. n-Butyl iodide (31.397 g, 170.617 mmol, 1.2 eq) was added over 5 minutes at −40° C., then the mixture was warmed to room temperature overnight and ether (350 mL) was added. The mixture was extracted with 0.1N hydrochloric acid (4×350 mL). The acid extracts were neutralized with solid sodium bicarbonate and extracted with methylene chloride (6×700 mL). The organic extracts were dried (magnesium sulfate) and concentrated to give the title compound (14.7 g, 83%).

C.
2-Butyl-1-[[2-(trimethylsilyl)ethoxy]-methyl]-1H-imidazole

To the title B compound (4.160 g, 33.498 mmol, 1 eq) in tetrahydrofuran (83.7 mL, 0.4M) at 0° C., sodium hydride (1.125 g, 46.897 mmol, 1.4 eq) was added. The mixture was stirred at 0° C. for 30 minutes and at room temperature for 15 minutes. The reaction was cooled to 0° C. and 2-(trimethylsilyl)ethoxymethyl chloride (7.114 mL, 40.197 mmol, 1.2 eq was added. The mixture was warmed to room temperature and stirred for 0.5 hours. Saturated ammonium chloride was added and the liquid was extracted with ethyl acetate. The extracts were dried (magnesium sulfate) and concentrated. The residue was chromatographed on silica gel eluting with hexane:ethyl acetate: triethylamine (100:50:0.2) to give the title compound (5.430 g, 64%).

D.
4,5-Dibromo-2-butyl-1-[[2-(trimethylsilyl)-ethoxy]methyl]-1H-imidazole

To the title C compound (6.466 g, 25.412 mmol, 1 eq) in chloroform (50.8 mL, 0.5M) at 0° C., bromine (2.669 mL, 52.094 mmol, 2.05 eq) in chloroform (50.8 mL, 1.04M) was added dropwise. The reaction was warmed to room temperature and stirred for two hours. The reaction mixture was neutralized with cool potassium carbonate water solution and extracted with methylene chloride. The extracts were dried (magnesium sulfate) and concentrated. The residue was chromatographed on silica gel eluting with hexane:ethyl acetate: triethylamine (100:5:0.15) to give the title compound (7.15 g, 68%).

E. [4-Bromo-2-butyl -1-[[2-(trimethylsilyl)-ethoxy]methyl]-1H-imidazol-5-yl]phosphonic acid, diethyl ester To the title D compound (3.246 g, 7.874 mmol, eq) in tetrahydrofuran (31.5 mL, 0.25M) at −78° C., n-butyl lithium (2.39M in hexane, 3.62 mL, 8.661 mmol, 1.1 eq) was added. The mixture was stirred at −78° C. for 5 minutes. Diethyl chlorophosphate (1.365 mL, 9.45 mmol, 1.2 eq) was added. The reaction was stirred at −78° C. for 10 minutes and at room temperature for 1 hour. Saturated ammonium chloride water solution was added. The mixture was extracted with methylene chloride. The extracts were washed with brine, dried (magnesium sulfate) and concentrated. The residue was chromatographed on silica gel eluting with chloroform:ethyl acetate:triethylamine (80:10:0.2) to give the title compound (2.266 g, 61%).

F. (4-Bromo-2-butyl-1H-imidazol-5-yl)phosphonic acid, diethyl ester

A mixture of the title E compound (1.020 g, 2.173 mmol), ethanol (20 mL) and 3N hydrochloric acid (20 mL) was heated at 50° C. for 2 hours and 15 minutes. The reaction mixture was neutralized with solid sodium bicarbonate and sodium bicarbonate water solution and then was extracted with ethyl acetate. The extracts were dried (magnesium sulfate) and concentrated to give the title compound (703 mg, 95%).

G.
[4-Bromo-2-butyl-1-[[1-(2-cyanophenyl)-1H-indol-4-yl]methyl]-1H-imidazol-5-yl]-phosphonic acid, diethyl ester To the title F compound (673 mg, 1.984 mmol, 1 eq) and 2-[4-(bromomethyl)-1H-indol-1-yl]-benzonitrile (710 mg, 2.282 mmol, 1.15 eq as prepared in part G.5 of Example 1) in dimethylformamide (8 mL, 0.25M), cesium carbonate (1616 mg, 4.96 mol, 2.5 eq) was added. The reaction was stirred overnight, diluted with ethyl acetate and filtered. The filtrate was washed with saturated ammonium chloride, and saturated sodium chloride and concentrated. The residue was chromatographed on silica gel eluting with toluene:ether:triethylamine (60:40:0.2) to give the title compound (660 mg, 58%).

H.
[4-Bromo-2-butyl-1-[[1-[2-(2H-tetrazol-5-yl)-phenyl]-1H-indol-4-yl]methyl]-1H-imidazol-5-yl]phosphonic acid, diethyl ester and
[4-Bromo-2-butyl-1-[[1-[2-(2H-tetrazol-5-yl)-phenyl]-1H-indol-4-yl]methyl]-1H-imidazol-5-yl]phosphonic acid, monoethyl ester A mixture of the title G compound (660 mg, 1.159 mmol), tributyltinazide (3 mL) and xylene (3 mL) was stirred at 90° C. for 24 hours. The reaction mixture was chromatographed on silica gel eluting with hexane:acetic acid (100:1) and then methylene chloride:ethyl acetate:acetic acid (100:50:0.3) to give [4-Bromo-2-butyl-1-[[1-[2-(2H-tetrazol-5-yl)phenyl]-1H-indol-4-yl]methyl]-1H-imidazol-5-yl]-phosphonic acid, diethyl ester (360 mg, 51%). The column was then eluted with ethyl acetate:acetic acid pyridine:water (4:1:1:0.5) to give [4-Bromo-2-butyl-1-[[1-[2-(2H-tetrazol-5-yl)phenyl]-1H-indol-4-yl]methyl]-1H-imidazol-5-yl]phosphonic acid, monoethyl ester (100 mg, 15%).

I.
[4-Bromo-2-butyl-1-[[1-[2-(2H-tetrazol-5-yl)phenyl]-1H-indol-4-yl]methyl]-1H-imidazol-5-yl]phosphonic acid, monoethyl ester, dipotassium salt

[4-Bromo-2-butyl-1-[[1-[2-(2H-tetrazol-5-yl)phenyl]-1H-indol-4-yl]methyl]-1H.-imidazol-5-yl]phosphonic acid, monoethyl ester (107 mg, 0.183 mmol) was dissolved in ethanol (20 mL), and potassium hydroxide water solution (1N, 0.549 mL, 0.549 mmol, 3.0 eq) was added. The reaction was stirred for 10 minutes. Most of the solvents were evaporated. The residue was chromatographed on an HP-20 column eluting with water, then water: acetone (100:5~40) to give the title compound (100 mg, 83%).

EXAMPLE 3

[4-Bromo-2-butyl-1-[[1-[2-(2H-tetrazol-5-yl)phenyl]-1H-indol-4-yl]methyl]-1H-imidazol-5-yl]phosphonic acid, trilithium salt Trimethylsilyl bromide (870 mg, 5.683 mmol, 25.0 eq) was added to a solution of [4-Bromo-2-butyl-1-[[1-[2-(2H-tetrazol-5-yl)phenyl]-1H-indol-4-yl]methyl]-1H-imidazol-5-yl]phosphonic acid, diethyl ester (137 mg, 0.224 mmol, 1 eq; from Example 2) in methylene chloride (2.4 mL, 0.093M). The mixture was stirred at room temperature for 64 hours. The remaining trimethylsilyl bromide and the solvent of the reaction were evaporated under vacuum. Methanol (2 mL) was added and the reaction was stirred for one hour. Then a lithium hydroxide water solution (1N, 1.344 mL, 6 eq) was added and the mixture was stirred for 20 minutes Most of the solvents were evaporated under vacuum. The residue was chromatographed on an HP-20 column eluting with water, then water:acetone (100:3) to give the title compound (110 mg, 86%).

EXAMPLE 4

[2-Butyl-4-chloro-1-[[1-[2-(2H-tetrazol-5-yl)phenyl]-1H-imidazol-5-yl]phosphonic acid, monoethyl ester, dipotassium salt A.
2-Butyl-4,5-dichloro-1-[[2-(trimethylsilyl)-ethoxy]methyl]-1H-imidazole To the title C compound of Example 2 (4.6 g, 18.078 mmol, 1 eq) in carbon tetrachloride (181 mL, 0.1M), N-chlorosuccinimide (4.949 g, 37.060 mmol, 2.05 eq) was added and the mixture was stirred at 40°–43° C. for 8 hours. Methylene chloride (180 mL) was added. The mixture was washed with water, dried over magnesium sulfate and concentrated in vacuo. The residue was chromatographed on silica gel eluting with hexane:ethyl acetate:triethylamine (100:5:0.1) to give the title compound (3.47 g, 59%).

B.
[2-Butyl-4-chloro-1-[[2-(trimethylsilyl)-ethoxy]methyl]-1H-imidazol-5-yl]phosphonic acid, diethyl ester To the title A compound (3.376 g, 10.441 mmol, 1 eq) and N,N,N′,N′-tetramethylethylene diamine (2.427 mL, 20.882 mmol, 2 eq) in tetrahydrofuran at −78° C., t-butyl lithium (1.7M in pentane, 6.756 mL, 11.485 mmol, 1.1 eq) was added dropwise. The mixture was stirred at −78° C. for 20 minutes. Diethyl chlorophosphate (2.162 g, 12.529 mmol, 1.2 eq) was added dropwise. The reaction was stirred at −78° C. for 10 minutes and then at room temperature for one hour. A solution of ammonium chloride/water was added and the mixture was extracted with methylene chloride. The extracts were dried (magnesium sulfate) and concentrated. The residue was chromatographed on silica gel eluting with methylene chloride:ethyl acetate:triethylamine (12:1:0.02) to give the title compound (3.486 g, 79%).

C. (2-Butyl-4-chloro-1H-imidazol-5-yl)-phosphonic acid, diethyl ester

A mixture of the title B compound (3.486 g, 8.203 mmol), ethanol (90 mL) and 3N hydrochloric acid (90 mL) was heated at 50° C. for 4 hours and 40 minutes. The reaction mixture was neutralized with solid sodium bicarbonate and a sodium bicarbonate/water solution, and then extracted with methylene chloride. The extracts were dried (magnesium sulfate) and concentrated to give the title compound (2.4 g, 99%).

D. [2-Butyl-4-chloro-1-[[1-(2-cyanophenyl)-1H-indol-4-yl]methyl]-1H-imidazol-5-yl]-phosphonic acid, diethyl ester To the title C compound (800 mg, 2.714 mmol, 1 eq) and 2-[4-(bromomethyl)-1H-indol-1-yl]-benzonitrile (971 mg, 3.122 mmol, 1.15 eq; the title G.5 compound of Example 1) in dimethylformamide (10.9 mL, 0.25M), cesium carbonate-(2.211 g, 6.785 mmol, 2.5 eq) was added. The reaction was stirred overnight, diluted with ethyl acetate and filtered. The filtrate was washed with saturated ammonium chloride, and saturated sodium chloride and concentrated. The residue was chromatographed on silica gel eluting with toluene:ether: triethylamine (65:35:0.2) to give the title compound (926 mg, 65%).

E. [2-Butyl-4-chloro-1-[[1-[2-(2H-tetrazol-5-yl)phenyl]-1H-indol-4-yl]methyl]-1H-imidazol-5-yl]phosphonic acid, diethyl ester and [2-Butyl-4-chloro-1-[[1-[2-(2H-tetrazol-5-yl)phenyl]-1H-indol-4-yl]methyl]-1H-imidazol-5-yl]phosphonic acid, monoethyl ester A mixture of the title D compound (996 mg, 1.897 mmol), tributyltinazide (5.5 mL) and xylene (5.5 mL) was stirred at 90° C. for 34 hours. The reaction mixture was chromatographed on silica gel eluting with hexane:acetic acid (100:1) and then methylene chloride:methanol:acetic acid (100:2.5:0.1) to give [2-Butyl-4-chloro-1-[[1-[2-(2H-tetrazol-5-yl)phenyl]-1H-indol-4-yl]methyl]-1H-imidazol-5-yl]phosphonic acid, diethyl ester (158 mg, 16%). The column was then eluted with ethyl acetate:acetic acid:pyridine:water (4:1:1:0.5) to give [2-Butyl-4-chloro-1-[[1-[2-(2H-tetrazol-5-yl)phenyl]-1H-indol-4-yl]methyl]-1H-imidazol-5-yl]phosphonic acid, monoethyl ester (126 mg, 13%).

F. [2-Butyl-4-chloro-1-[[1-[2-(2H-tetrazol-5-yl)phenyl]-1H-indol-4-yl]methyl]-1H-imidazol-5-yl]phosphonic acid, monoethyl ester, dipotassium salt

[2-Butyl-4-chloro-1-[[1-[2-(2H-tetrazol-5-yl)phenyl]-1H-indol-4-yl]methyl]-1H-imidazol-5-yl]-phosphonic acid, monoethyl ester (126 mg, 0.234 mmol) was dissolved in ethanol (30 mL) and water (1 mL) and a solution of potassium hydroxide/water (1N, 1.6 mL, 1.6 mmol, 6.84 eq) was added. The reaction was stirred for 15 minutes. Most of the solvents were evaporated under vacuum. The residue was chromatographed on an HP-20 column eluting with water, then water:acetone (100:12~40) to give the title compound (108 mg, 75%).

EXAMPLE 5

[2-Butyl-4-chloro-1-[[1-[2-(2H-tetrazol-5-yl)-phenyl]-1H-indol-4-yl]methyl]-1H-imidazol-5-yl]-phosphonic acid, monomethyl ester, dipotassium salt

A
[2-Butyl-4-chloro-1-[[2-(trimethylsilyl)-ethoxy]methyl]-1H-imidazol-5-yl]phosphonic acid, dimethyl ester To the title A compound of Example 4 (970 mg, 3 mmol, 1 eq.) and N,N,N',N'-tetramethylethylenediamine (697 mg, 6 mmol, 2 eq.) in tetrahydrofuran (12 mL, 0.25M) at −78° C., t-BuLi (1.7M in pentane, 1.94 mL, 3.3 mmol, 1.1 eq.) was added dropwise. The mixture was stirred at −78° C. for 20 minutes. ClPO(OMe)2 (520 mg, 3.6 mmol, 1 eq) was added dropwise. The reaction was stirred at −78° C. for three hours and at room temperature for one hour. A solution of ammonium chloride/water was added and the mixture was extracted with methylene chloride. The extracts were dried (magnesium sulfate) and concentrated. The residue was chromatographed on silica gel eluting with chloroform:ethyl acetate:triethylamine (90:10:0.2) to give the title compound.

B. [2-Butyl-4-chloro-1H-imidazol-5-yl]-phosphonic acid, dimethyl ester

A mixture of the title A compound (374 mg, 0.94 mmol), ethanol (15 mL) and 3N hydrochloric acid (15 mL) was heated at 55° C. for three hours and 30 minutes. The mixture was neutralized with solid sodium bicarbonate, and extracted with methylene chloride. The extracts were dried and concentrated to give the title compound (250 mg, 100%).

C.
[2-Butyl-4-chloro-1-[[1-[2-[2-(triphenyl-methyl)-2H-tetrazol-5-yl]phenyl]-1H-indol-4-yl]methyl]-1H-imidazol-5-yl]phosphonic acid, dimethyl ester To the title B compound (250 mg, 0.94 mmol, 1 eq.) and the title C compound of Example 8 (4-Bromomethyl)-1-[2-[2-(triphenylmethyl-2H-tetrazol-5-yl]phenyl]-1H-indole)(618 mg, 1.04 mmol, 1.1 eq.) in dimethylformamide (3.8 mL, 0.25M), cesium carbonate (767 mg, 2.36 mmol, 2.5 eq.) was added. The reaction was stirred at room temperature overnight and at 50° C. for two hours, diluted with ethyl acetate and filtered. The filtrate was washed with saturated ammonium chloride, dried (magnesium sulfate) and concentrated. The residue was chromatographed on silica gel eluting with toluene:ether:triethylamine (80:20:0.2) to give the title compound (321 mg, 44%).

D.

[2-Butyl-4-chloro-1-[[1-[2-(2H-tetrazol-5-yl)phenyl]-1H-indol-4-yl]methyl]-1H-imidazol-5-yl]phosphonic acid, dimethyl ester The title C compound was dissolved in ethanol (4 mL) and tetrahydrofuran (4 mL), and a hydrochloric acid water solution (10%, 4 mL) was added. The reaction was stirred for four hours and 30 minutes and concentrated. The residue was chromatographed on silica gel eluting with methylene chloride:methanol:acetic acid (100:2.5:0.2) to give the title compound (171 mg, 77%).

E.

[2-Butyl-4-chloro-1-[[1-[2-(2H-tetrazol-5-yl)phenyl]-1H-indol-4-yl]methyl]-1H-imidazol-5-yl]phosphonic acid, monomethyl ester, dipotassium salt The title D compound (171 mg, 0.32 mmol, 1 eq.) was dissolved in methanol (2 mL) and water (0.73 mL). A solution of potassium hydroxide/water (1N, 1.3 mL, 1.3 mmol, 4 eq.) was then added. The mixture was heated at 47° C. overnight. Most solvents of the mixture were evaporated under vacuum. The residue was chromatographed on an HP-20 column eluting with water, and then water:acetone (100:3) to give the title compound (134 mg, 70%); m.p. >240° C.

| Elemental Analysis (%) for 2.2 H$_2$O | | | | |
|---|---|---|---|---|
| Cal'c: C 44.92; | H 4.30; | N 15.28; | Cl 5.52; | P 4.83; |
| Found: C 45.24; | H 4.23; | N 15.04; | Cl 5.14; | P 4.72. |

EXAMPLE 6

[2-Butyl-4-chloro-1-[[1-[2-(2H-tetrazol-5-yl)-phenyl]-1H-indol-4-yl]methyl]-1H-imidazol-5-yl]phosphonic acid, trilithium salt Trimethylsilyl bromide (974 mg, 6.364 mmol, 23 eq) was added to a solution of [2-Butyl-4-chloro-1-[[1-[2-(2H-tetrazol-5-yl)phenyl]-1H-indol-4-yl]-methyl]-1H-imidazol-5-yl]phosphonic acid, diethyl ester (158 mg, 0.278 mmol, 1 eq) in methylene chloride (3 mL, 0.093M). The mixture was stirred at 35° C. for 20 hours. The remaining trimethylsilyl bromide and the solvent of the reaction were evaporated under vacuum. Methanol (3 mL) was added and the reaction was stirred for 1 hour. A lithium hydroxide water solution (1N, 1.668 mL, 6 eq) was added and the mixture was stirred for 20 minutes. Most of the solvents were evaporated under vacuum. The residue was chromatographed on an HP-20 column eluting with water, then water:acetone (100:3) to give the title compound (120 mg, 81%).

EXAMPLE 7

[4-chloro-2-propyl-1-[[1-[2-(2H-tetrazol-5-yl)-phenyl]-1H-indol-4-yl]methyl]-1H-imidazol-5-yl]phosphonic acid, trilithium salt Trimethylsilylbromide (2.78 g, 18.2 mmol, 17 eq.) was added to a solution of the title G compound of Example 10 (585 mg, 1.06 mmol, 1 eq.) in methylene chloride (10 mL, 0.1M ). The mixture was stirred at 35° C. for 24 hours. The remaining trimethylsilylbromide and the solvent of the reaction were evaporated under vacuum. Methanol (10 mL) was added and the reaction was stirred for one hour. Then a lithium hydroxide water solution (1N, 6.4 mL, 6 eq.) was added and the mixture was stirred for 20 minutes. Most of the solvents were evaporated under vacuum. The residue was chromatographed on an HP-20 column eluting with water to give the title compound (410 mg, 75%); m.p. >250° C.

| Elemental Analysis (%) for 1.3 H$_2$O | | | | |
|---|---|---|---|---|
| Cal'c: C 49.02; | H 3.85; | N 18.19; | Cl 6.58; | P 5.75; |
| Found: C 48.70; | H 3.44; | N 17.82; | Cl 6.32; | P 5.58. |

EXAMPLE 8

[2-Butyl-4-chloro-1-[[1-[2-(2H-tetrazol-5-yl)phenyl]-1H-indol-4-yl]methyl]-1H-imidazol-5-yl]phosphonic acid, diethyl ester, monopotassium salt

A.

1-[2-[2-(Triphenylmethyl)-2H-tetrazol-5-yl]phenyl]-1H-indole-4-carboxylic acid, methyl ester An initially heterogeneous mixture of the title 2 compound of Example 1G (1-(2-Cyanophenyl)-1H-indole-4-carboxylic acid, methyl ester; 8 g, 29 mmol) tri-n-butyl-tin azide (14.6 g, 44 mmol) and xylenes (20 mL) was heated at 130° C. overnight in a stoppered flask. The cooled reaction mixture was next concentrated in vacuo and treated with methanol (20 mL) and acetic acid (20 mL) for three hours, then concentrated again in vacuo and the acetic acid removed by evaporation with toluene. To the resulting crude reaction mixture was added triphenylmethyl chloride (10.5 g, 37.7 mmol), triethylamine (8.1 mL, 58.1 mmol) and acetone (110 mL) and the stoppered solution was stirred at room temperature for two days. After removing the acetone in vacuo, the product was partitioned between methylene chloride and half-saturated brine. The organic extract was rinsed with brine, dried (magnesium sulfate) and concentrated. Trituration with ethyl acetate/hexanes gave the title compound (15.79 g, 97%).

B.

1-[2-[2-(Triphenylmethyl)-2H-tetrazol-5-yl]phenyl]-1H-indole-4-methanol

The title A compound (15.7 g, 28 mmol) was dissolved in anhydrous tetrahydrofuran (140 mL) and cooled to 0° C., then treated with a 1M solution of lithium aluminum hydride in tetrahydrofuran (65 mL, 65 mmol). After three hours at 0° C., TLC of a reaction aliquot showed absence of starting material. The reaction was carefully quenched at 0° C. by addition sequentially of water (2.6 mL), sodium hydroxide (2.6 mL, 15% aq.) and water (7.9 mL). The resulting mixture was diluted with ethyl acetate, filtered over Celite, dried (magnesium sulfate) and concentrated. Trituration with ethyl acetate/hexanes yielded the title compound (13.35 g, 89%).

C.

4-(Bromomethyl)-1-[2-[2-(triphenylmethyl-2H-tetrazol-5-yl)phenyl]-1H-indole

To a mixture of the title B compound (2.73 g, 5.12 mmol) and carbon tetrabromide (2.38 g, 7.16 mmol) in methylene chloride (20 mL) cooled to 0° C. was added triphenylphosphine (1.74 g, 6.65 mmol). After 30 minutes, the reaction was allowed to warm to room temperature and stirred for another four hours, then concentrated in vacuo and triturated with methylene chloride/hexanes to afford a crude material (2.46 g). Trituration again with methylene chloride/hexanes yielded the title compound (1.34 g), and trituration of the accompanying mother liquor with acetone/hexanes gave another 1.05 g of product. Total yield of the title compound was 2.39 g (78%) with acceptable purity.

D.
[2-Butyl-4-chloro-1-[[1-[2-[2-(triphenyl-methyl)-2H-tetrazol-5-yl]phenyl]-1H-indol-4-yl]methyl]-1H-imidazol-5-yl]phosphonic acid, diethyl ester To the title C compound of Example 4 (400 mg, 1.357 mmol, 1 eq.) and the title C compound (891 mg, 1.493 mmol, 1.1 eq.) in dimethylformamide (5.4 mL, 0.25M), cesium carbonate (1.105 g, 3.393 mmol, 2.5 eq.) was added. The reaction was stirred at room temperature overnight and then heated at 50° C. for two hours, diluted with ethyl acetate and filtered. The filtrate was washed with saturated ammonium chloride, and saturated sodium chloride and concentrated. The residue was chromatographed on silica gel eluting with toluene:ether:triethylamine (80:20:0.2) to give the title compound (660 mg, 60%).

E.
[2-Butyl-4-chloro-1-[[1-[2-(2H-tetrazol-5-yl)phenyl]-1H-indol-4-yl]methyl]-1H-imidazol-5-yl]phosphonic acid, diethyl ester To the title D compound (709 mg, 0.875 mmol) in tetrahydrofuran (7 mL) and ethanol (7 mL), hydrochloric acid water solution (7 mL, 10%) was added. The reaction was stirred for four hours. The mixture was concentrated in vacuo and the residue was chromatographed on silica gel eluting with methylene chloride:methanol:acetic acid (100:2.5:0.15) to give the title compound (400 mg, 80%).

F.
[2-Butyl-4-chloro-1-[[1-[2-(2H-tetrazol-5-yl)phenyl]-1H-indol-4-yl]methyl]-1H-imidazol-5-yl]phosphonic acid, diethyl ester, monopotassium salt To the title E compound (150 mg, 0.264 mmol, 1 eq.) in ethanol (20 mL), a solution of potassium bicarbonate (53 mg, 0.528 mmol, 2 eq.) in water (4 mL) was added. The reaction was stirred for 35 minutes. Most solvents of the mixture were evaporated in vacuo and the residue was chromatographed on an HP-20 column eluting with water, then water/acetone (100:10~30) to give the title compound (135 mg, 84%).

EXAMPLE 9

[2-Butyl-1-[[1-[2-(2H-tetrazol-5-yl)phenyl]-1H-indol-4-yl]methyl]-1H-imidazol-5-yl]phosphonic acid, monoethyl ester, dipotassium salt A.
[2-Butyl-1-[[1-[2-(2H-tetrazol-5-yl)phenyl]-1H-indol-4-yl]methyl]-1H-imidazol-5-yl]-phosphonic acid, diethyl ester A mixture of the title E compound of Example 8 (260 mg, 0.458 mmol, 1 eq.), 10% palladium on charcoal (260 mg, 100% by Wt.), 1N potassium hydroxide (0.915 mL, 0.915 mmol, 2 eq.) and ethanol (26 mL) was stirred under hydrogen for ten hours. The palladium on charcoal was removed by filtration. The filtrate was concentrated and the residue was chromatographed on silica gel eluting with methylene chloride:methanol:acetic acid (100:5:0.15) to give the title compound (170 mg, 70%).

B.
2-Butyl-1-[[1-[2-(2H-tetrazol-5-yl)phenyl]-1H-indol-4-yl]methyl]-1H-imidazol-5-yl]-phosphonic acid, monoethyl ester, dipotassium salt The title A compound (175 mg, 0.328 mmol, 1 eq.) was dissolved in ethanol (0.98 mL) and a solution of potassium hydroxide in water (1N, 0.98 mL, 0.98 mmol, 3 eq.) was added. The reaction was stirred at 50° C. for five days and then at 70° C. for one day. An additional solution of potassium hydroxide water (1N, 0.33 mL, 0.33 mmol, 1 eq.) was added after four days. Most of the solvents were evaporated under vacuum. The residue was chromatographed on an HP-20 column eluting with water, then water:acetone (100:5~7) to give the title compound (158 mg, 83%).

EXAMPLE 10

[4-Chloro-2-propyl-1-[[1-[2-(2H-tetrazol-5-yl)-phenyl]-1H-indol-4-yl]methyl]-1H-imidazol-5-yl]-phosphonic acid, monoethyl ester, dipotassium salt A. 2-Propyl-1H-imidazole To the title A compound of Example 2 (16.3 g, 103 mmol, 1 eq.) in dry tetrahydrofuran (259 mL, 0.4M) at −40° C. was added via syringe n-butyl lithium (2.5M in hexane, 41.5 mL, 103 mmol, 1 eq.) such that the temperature did not rise above −35° C. The mixture was stirred at −40° C. for 15 minutes. n-Propyl iodide (21.15 g, 124 mmol, 1.2 eq.) was added over five minutes at −40° C. Then the mixture was warmed to room temperature overnight, and ether (260 mL) was added. The mixture was extracted with 0.1N hydrochloric acid (4×260 mL). The acid extracts were neutralized with solid sodium bicarbonate, concentrated and extracted with methylene chloride. The organic extracts were dried (magnesium sulfate) and concentrated to give the title A compound (10.9 g, 95%).

B.
2-Propyl-1-[[2-(trimethylsilyl)ethoxy]-methyl]-1H-imidazole

To the title A compound (202 mg, 1.83 mmol, 1 eq.) in tetrahydrofuran (4.6 mL, 0.4M) at 0° C., sodium hydride (61.5 mg, 2.562 mmol, 1.4 eq.) was added. The mixture was stirred at 0° C. for 30 minutes and at room temperature for 15 minutes. The reaction was cooled to 0° C. and 2-(trimethyl)-ethoxymethyl chloride (0.39 mL, 2.196 mmol, 1.2 eq.) was added. The mixture was warmed to room temperature and stirred for 30 minutes. Saturated ammonium chloride was added and the liquid was extracted with ethyl acetate. The extracts were dried (magnesium sulfate) and concentrated. The residue was chromatographed on silica gel eluting with hexane:ethyl acetate:triethylamine (40:60:0.2) to give the title compound (130 mg, 30%).

C.
4,5-Dichloro-2-propyl-1-[[2-(trimethylsilyl)-ethoxy]methyl]-1H-imidazole

To the title B compound (4.08 g, 16.97 mmol, 1 eq.) in carbon tetrachloride (170 mL, 0.1M), N-chlorosuccinimide (4.645 g, 34.7 mmol, 2.05 eq.) was added and the mixture was stirred at 35°~37° C. for 24 hours. Carbon tetrachloride (230 mL) was added and the mixture was stirred for ten minutes. The solids were removed by filtration. The filtrate was concentrated and the residue was chromatographed on silica gel eluting with hexane:ethyl acetate:triethylamine (20:1:0.02) to give the title compound (2.85 g, 54%).

D.

[4-Chloro-2-propyl-1-[[2-(trimethylsilyl)-ethoxy]methyl]-1H-imidazol-5-yl]phosphonic acid, diethyl ester To the title C compound (1.355 g, 4.380 mmol, 1 eq.) and N,N,N',N'-tetramethylethylenediamine (1.32 mL 8.761 mmol, 2 eq.) in tetrahydrofuran at −78° C., t-butyl lithium (1.7M in pentane, 2.83 mL, 4.818 mmol, 1.1 eq.) was added dropwise. The mixture was stirred at −78° C. for 20 minutes. Diethyl chlorophosphate (0.76 mL, 5.256 mmol, 1.2 eq.) was added dropwise. The reaction was stirred at −78° C. for ten minutes and then at room temperature for one hour. A solution of ammonium chloride/water was added and the mixture was extracted with methylene chloride. The extracts were dried (magnesium sulfate) and concentrated. The residue was chromatographed on silica gel eluting with chloroform:ethyl acetate:triethylamine (100:10:0.2) to give the title compound (1.547 g, 86%).

E. (4-Chloro-2-propyl-1H-imidazol-5-yl)-phosphonic acid, diethyl ester

A mixture of the title D compound (1.547 g, 3.764 mmol), ethanol (50 mL) and 3N hydrochloric acid (50 mL) was heated at 50° C. for 4.5 hours. The reaction was neutralized with solid sodium bicarbonate and sodium bicarbonate/water solution, and extracted with methylene chloride. The extracts were dried (magnesium sulfate) and concentrated to give the title compound (1.06 g, 100%)

F.
[4-Chloro-2-propyl-1-[[1-[2-[2-(triphenyl-methyl)-2H-tetrazol-5-yl]phenyl]-1H-indol-4-yl]methyl]-1H-imidazol-5-yl]-phosphonic acid, diethyl ester To the title E compound (281 mg, 1 mmol, eq. and the title C compound of Example 8 (656 mg, 1.1 mmol, 1.1 eq.) in dimethylformamide (4 mL, 0.25M), cesium carbonate (815 mg, 2.5 mmol, 2.5 eq.) was added. The reaction was stirred overnight at room temperature, diluted with ethyl acetate and filtered. The filtrate was washed with saturated ammonium chloride and saturated sodium chloride and concentrated. The residue was chromatographed on silica gel eluting with toluene:ether:triethylamine (80:20:0.2) to give the title compound (480 mg, 60%).

G.
[4-Chloro-2-propyl-1-[[1-[2-(2H-tetrazol-5-yl)phenyl]-1H-indol-4-yl]methyl]-1H-imidazol-5-yl]phosphonic acid, diethyl ester To the title F compound (480 mg, 0.603 mmol) in ethanol (7 mL) and tetrahydrofuran (7 mL), hydrochloric acid (10% in water, 7 mL) was added. The reaction was stirred at room temperature for 3.5 hours and then concentrated under vacuum. The residue was chromatographed on silica gel eluting with methylene chloride: methanol:acetic acid (100:2.5:0.2) to give the title compound (280 mg, 84%).

H.
[4-Chloro-2-propyl-1-[[1-[2-(2H-tetrazol-5-yl)phenyl]-1H-indol-4-yl]methyl]-1H-imidazol-5-yl]phosphonic acid, monoethyl ester, dipotassium salt The title G compound (280 mg, 0.505 mmol, eq.) was dissolved in ethanol (2 mL) and a solution of potassium hydroxide/water (1N, 2.0 mL, 2.0 mmol, 4 eq.) was added. The mixture was heated at 70° C. for 40 hours and at 75° C. for 1.5 hours. Additional potassium hydroxide/water (1N, 0.25 mL, 0.5 eq.) was added after 24 hours and another portion of potassium hydroxide/water (1N, 0.5 mL, 1 eq.) was added after 40 hours. Most solvents of the reaction were evaporated in vacuo. The residue was chromatographed on an HP-20 column eluting with water and water:acetone (100:5) to give the title compound (280 mg, 92%).

EXAMPLE 11

[2-Butyl-4-bromo-1-[[1-[2-(2H-tetrazol-5-yl)phenyl]-1H-indol-4-yl]methyl]-1H-imidazol-5-yl]methyl-phosphonic acid, dilithium salt A [4-Bromo-2-butyl-1-[[2-(trimethylsilyl)-ethoxy]methyl]-1H-imidazol-5-yl]phosphinic acid A 2.5M solution of n-butyl lithium in hexanes (1.64 mL, 4.1 mmol) was added dropwise over a five minute period to a tetrahydrofuran (4 mL) solution of the title D compound of Example 2 at −78° C. The reaction mixture was stirred for ten minutes, diethylchlorophosphite (0.59 ml 4.1 mmol) was added dropwise at −78° C. and the reaction mixture was stirred at ambient temperature (−78° C. to 0° C.) for two hours. 2N for 30 minutes, and 2N sodium hydroxide (8 mL) was added. After two hours the reaction was diluted with water (15 mL) and washed with ether (2×, 10 mL). The aqueous solution was acidified with 2N hydrochloric acid to pH=2 and product was extracted with three portions of ether (100 mL). The ether extracts were washed with water, brine, dried (sodium sulfate), filtered, and concentrated in vacuo to yield the title compound (0.86 g, 70%)

B.
[4-Bromo-2-butyl-1-[[2-(trimethylsilyl)-ethoxy]methyl]-1H-imidazol-5-yl]-methylphosphinic acid, methyl ester Cesium carbonate (2.38 g, 7.3 mmol) and methyl iodide (1.04 g, 7.3 mmol) were added to a solution of the title A compound (0.86 g, 2.16 mmol) in dimethylformamide (8 mL). The reaction mixture was stirred at room temperature overnight, diluted with ether (200 mL) and washed with water(2×), brine, dried (sodium sulfate), filtered, and concentrated in vacuo. Product was chromatographed through Merck silica gel (50 g) using a 1:1 ethyl acetate:hexane solvent system. The appropriate fractions were combined and concentrated to yield the title compound (0.4 g, 44%).

C.
(4-Bromo-2-butyl-1H-imidazol-5-yl)-methylphosphinic acid, methyl ester

The title B compound was stirred overnight at 50° C. in a 1:1 solution of methanol:3N hydrochloric acid. Solid sodium bicarbonate was added and product was extracted with chloroform (2×, 100 mL). The chloroform was washed with water, brine, dried (sodium sulfate), filtered and concentrated in vacuo to yield the title compound (0.2 g, 99%).

D.
[4-Bromo-2-butyl-1-[[1-[2-[2-(triphenyl-methyl)-2H-tetrazol-5-yl]phenyl]-1H-indol-4-yl]methyl]-1H-imidazol-5-yl]-methylphosphinic acid, methyl ester Cesium carbonate (0.57 g, 1.75 mmol) was added to a dimethylformamide (2.7 mL) solution of the title C compound (0.207 g, 0.7 mmol) and the title C compound of Example 8 (0.44 g, 0.74 mmol) and stirred at room temperature for 60 hours then at 50° C. for two hours. The reaction mixture was diluted with water (10 mL) and product was extracted with ethyl acetate (3×, 100 mL). The ethyl acetate solution was washed with water, brine, dried (sodium sulfate), and concentrated in vacuo. Product was chromatographed through Merck silica gel (50 g) using a 3:7 ethyl acetate:toluene solvent system. The appropriate fractions were combined and concentrated to yield the title compound (0.27 g, 47%).

E.

[4-Bromo-2-butyl-1-[[1-[2-(2H-tetrazol-5-yl)-phenyl]-1H-indol-4-yl]methyl]-1H-imidazol-5-yl]methylphosphinic acid, methyl ester The title D compound was dissolved in a solution of tetrahydrofuran:formic acid:water (4.5 mL, 2:2:0.5) and stirred at room temperature for six hours. The reaction mixture was diluted with water (5 mL) and the pH was adjusted to 3 with aqueous bicarbonate. Product was extracted with ethyl acetate (3×, 60 mL) and the ethyl acetate extract was concentrated in vacuo and chromatographed through Merck silica gel (80 g) using a (3:47) methanol:chloroform solvent system. The appropriate fractions were combined and concentrated to yield the title compound (0.13 g, 76%).

F.

[2-Butyl-4-bromo-1-[[1-[2-(2H-tetrazol-5-yl)phenyl]-1H-indol-4-yl]methyl]-1H-imidazol-5-yl]methylphosphonic acid, dilithium salt Bromotrimethylsilane (0.05 mL) was added to a methylenechloride (1.5 mL) solution of the title E compound and the reaction mixture was stirred at 50° C. for six hours and at room temperature overnight. Water:dioxane (1 mL, 1:1) was added and after one hour the reaction mixture was concentrated in vacuo. The resulting residue was dissolved in 1N lithium hydroxide (0.6 mL), passed through a 25 mL column of HP-20 with water containing 5% acetone. The appropriate fractions were combined, concentrated, redissolved in water, filtered through a millipore, and lyophilized to yield the title compound (78.7 mg, 62%).

EXAMPLE 12

[2-Butyl-4-chloro-1-[1-[2-(2H-tetrazol-5-yl)-phenyl]-1H-indol-4-yl]methyl]-1H-imidazol-5-yl]methylphosphinic acid, dilithium salt

A.

[2-Butyl-4-chloro-1-[[2-(trimethylsilyl)ethoxy]-methyl]-1H-imidazol-5-yl]methylphosphinic acid, ethyl ester The title A compound of Example 4 (1.6 g, 5 mmol), and N,N,N',N'-tetramethylethylenediamine (0.92 mL, 6.1 mmol) were dissolved in tetrahydrofuran (15 mL), cooled to −78° C., and t-butyl lithium (3.6 mL, 6.1 mmol; 1.7M in hexanes) was added dropwise. After 20 minutes, diethylchlorophosphite (0.92 mL, 6.4 mmol) was added and the reaction mixture was stirred at ambient temperature (−78° C. to 0° C.) for three hours. The resulting solution was added to methyl iodide (20 mL), stoppered and heated at 45° C. for six hours. The reaction was quenched by the addition of water (200 mL) and product was extracted with ether (3×, 200 mL). The ether extracts were concentrated in vacuo and product was purified by chromatography through Merck silica gel (50 g) using a (2:8) ethyl acetate:Hexane solvent system. The appropriate fractions were combined and concentrated to give the title compound (0.62 g, 26%).

B.

(2-Butyl-4-chloro-1H-imidazol-5-yl]methylphosphinic acid, ethyl ester

The title A compound (530 mg, 1.34 mmol, 1.0 eq. was combined with ethanol (5.4 mL, 0.25M) and 10% hydrochloric acid (5.4 mL, 0.25M) and heated at 50° C. for four hours. The reaction was then cooled to room temperature and concentrated to remove most of the ethanol. Water and solid sodium bicarbonate were added till the reaction was slightly basic. The mixture was then extracted three times with methylene chloride. The combined organic extracts were dried over sodium sulfate, filtered through magnesium sulfate and concentrated to provide the title compound (357.8 mg, >100%).

C.

[2-Butyl-4-chloro-1-[[1-[2-[2-(triphenyl-methyl)-2H-tetrazol-5-yl]phenyl]-1H-indol-4-yl]methyl]-1H-imidazol-5-yl]methyl-phosphinic acid, ethyl ester The title B compound (355.2 mg, 1.34 mmol, 1.0 eq.) was combined with the title C compound of Example 8 (840.5 mg, 1.41 mmol, 1.05 eq.) and cesium carbonate (1.093 g, 3.36 mmol, 2.5 eq.) in dimethylformamide (5.36 mL, 0.25M) and stirred at room temperature overnight. The reaction was then diluted with ethyl acetate and filtered. The filtrate was washed with water and aqueous saturated sodium chloride. Next, the filtrate was dried over sodium sulfate, filtered through magnesium sulfate and concentrated. The residue was chromatographed on Merck silica gel (50 g) eluting with toluene-:acetone (10:1) to provide the title compound (585 mg, 56%).

D.

[2-Butyl-4-chloro-1-[[1-[2-(2H-tetrazol-5-yl)phenyl]-1H-indol-4-yl]methyl]-1H-imidazol-5-yl]methylphosphinic acid, ethyl ester The title C compound (581 mg, 0.744 mmol) was dissolved in a mixture of tetrahydrofuran (2 mL), formic acid (2 mL), and water (0.5 mL). The reaction mixture was stirred at room temperature in a stoppered flask. After 24 hours, TLC (silica gel; 9.4:0.6, chloroform:methanol) indicated remaining starting material. Reaction was continued for another 24 hours after which time the amount of remaining starting material seemed to be significantly reduced. TLC analysis showed minor byproducts. The crude reaction mixture was diluted with ethyl acetate (50 mL) and the pH was adjusted to 2 with aqueous potassium bicarbonate. Product was extracted with ethyl acetate (2×, 100 mL), and the ethyl acetate solution was washed with water (2×), brine and concentrated in vacuo. Crude title compound was chromatographed through Merck silica gel (80 g) using a (3:87) methanol:chloroform solvent system. The appropriate fractions were combined and concentrated to yield the title compound (0.29 g, 72%)

E.

[2-Butyl-4-chloro-1-[[1-[2-(2H-tetrazol-5-yl)-phenyl]-1H-indol-4-yl]methyl]-1H-imidazol-5-yl]methylphosphinic acid, dilithium salt Trimethylsilylbromide (0.14 mL, 1.0 mmol) was added to a methylene chloride solution of the title D compound (0.21 g, 0.42 mmol) and stirred at 35° C. for seven hours and at room temperature overnight. Water:dioxane solution (2 mL, 1:1) was added, stirred for one hour, concentrated in vacuo, and the reaction mixture was dissolved in 1N lithium hydroxide (1 mL). This solution was passed through HP-20 (100 mL) using water followed by 5% acetone in water. The appropriate fractions were combined, concentrated in vacuo, redissolved in water (30 mL), filtered through a millipore filter and lyophilized to yield the title compound (0.12 g, 55%)

What is claimed is:

1. A compound of the formula

[Structure I shown]

or a pharmaceutically acceptable salt or prodrug thereof;

where X is —N— or $$-\overset{R_{5'}}{\underset{|}{C}}-;$$

the broken line adjacent to the X atom represents the optional presence of a double bond, provided that if X is nitrogen, the double bond must be present;

$R_1$ is hydrogen, halogen, —$CF_3$ or —$CF_2CF_3$;

$R_2$ is hydrogen or $R_7$;

$R_3$ is hydroxy or $R_8$;

$R_4$ is alkyl, alkenyl or alkynyl or an alkyl, alkenyl or alkynyl group substituted with one or more F or —$CO_2R_9$ groups; cycloalkyl; (cycloalkyl)alkyl of 4 to 10 carbon atoms; (cycloalkyl)alkenyl or (cycloalkyl)alkynyl of 5 to 10 carbon atoms; —$NR_{12}R_{13}$; —$(CH_2)_nZ(CH_2)_pR_{15}$; benzyl or benzyl substituted with 1 or 2 halogens, alkoxy of 1 to 4 carbon atoms, alkyl of 1 to 4 carbon atoms, haloalkyl or nitro; —$SR_{16}$ or —$OR_{16}$;

$R_5$ and $R_{5'}$ are independently selected from hydrogen, alkyl, aryl, cycloalkyl, arylalkyl, haloalkyl, —$CO_2R_9$, —$NHSO_2CF_3$, —$\overset{O}{\underset{\|}{OS}}(OH)_2$, —$SO_3H$, —$C(CF_3)_2OH$, —$\overset{O}{\underset{\|}{OP}}(OH)_2$, —$PO_3H_2$, —$\overset{O}{\underset{\|}{NHP}}(OH)_2$, —$CONHSO_2CF_3$, [tetrazole structures], —$CH_2$—[tetrazole],

[additional heterocyclic structures including triazole with CF$_3$, —CONH—[tetrazole], —CONHOR$_{10}$, oxadiazolone structures with HC—R$_{10}$/OCOR$_{11}$ and HC—R$_{10}$/OCOOR$_{11}$, $-\overset{OH}{\underset{R_{17}}{\overset{|}{C}}}\overset{O}{\underset{\|}{P}}(OH)_2$ or [imidazole with R$_{18}$];

$R_6$ is an acid moiety such as hydrogen,

—$CO_2R_9$, —$NHSO_2CF_3$, —$\overset{O}{\underset{\|}{OS}}(OH)_2$, —$SO_3H$, —$C(CF_3)_2OH$, —$\overset{O}{\underset{\|}{OP}}(OH)_2$, —$PO_3H_2$, —$\overset{O}{\underset{\|}{NHP}}(OH)_2$, —$CONHSO_2CF_3$,

[tetrazole], —$CH_2$—[tetrazole], [triazole-CF$_3$],

—CONH—[tetrazole], —CONHOR$_{10}$, [oxadiazolone with HC—R$_{10}$/OCOR$_{11}$],

[oxadiazolone with HC—R$_{10}$/OCOOR$_{11}$], $-\overset{OH}{\underset{R_{17}}{\overset{|}{C}}}\overset{O}{\underset{\|}{P}}(OH)_2$ or [imidazole with R$_{18}$];

$R_7$ is alkyl of 1 to 6 carbon atoms, cycloalkyl of 3 to 6 carbon atoms, arylalkyl, alkylaryl or phenyl;

$R_8$ is alkyl of 1 to 6 carbon atoms, alkylaryl, cycloalkyl of 3 to 6 carbon atoms or $OR_7$;

$R_9$ is hydrogen, alkyl, perfluoroalkyl of 1 to 8 carbon atoms, cycloalkyl of 3 to 6 carbon atoms, phenyl, benzyl, —$\overset{}{\underset{R_{10}}{\overset{|}{CH}}}$—O—$COR_{11}$ or —$\overset{}{\underset{R_{10}}{\overset{|}{CH}}}$—O—$COOR_{11}$;

$R_{10}$ is hydrogen, alkyl, aryl, alkylaryl, arylalkyl or cycloalkyl;

$R_{11}$ is alkyl, aryl, alkylaryl, arylalkyl or cycloalkyl;

$R_{12}$ and $R_{13}$ are independently hydrogen, alkyl of 1 to 6 carbon atoms, benzyl, α-methylbenzyl, or taken together with the nitrogen atom to which they are attached form a ring of the formula

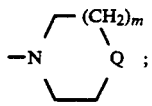

$R_{14}$ is hydrogen, alkyl of 1 to 6 carbon atoms, cycloalkyl of 3 to 6 carbon atoms, phenyl or benzyl;

$R_{15}$ is hydrogen; alkyl of 1 to 6 carbon atoms; cycloalkyl; alkenyl or alkynyl of 2 to 4 carbon atoms; or the above alkyl, cycloalkyl, alkenyl or alkynyl group optionally substituted with F or $-CO_2R_9$;

$R_{16}$ is alkyl, alkenyl, alkynyl, aryl, arylalkyl, cycloalkyl, (cycloalkyl)alkyl, heterocyclo, (heterocyclo)alkyl or haloalkyl;

$R_{17}$ is hydrogen, alkyl of 1 to 5 carbon atoms or phenyl;

$R_{18}$ is $-CN$, $-NO_2$ or $-CO_2R_9$;

Q is $-CH_2$, $-O-$, or $-NR_{10}$;

Z is $-O-$, $-S-$ or $-NR_{14}$;

m is 0, or the integer 1;

n is an integer of 1 to 5; and p is an integer of 1 to 5.

2. A compound of claim 1 wherein $R_1$ is hydrogen or halogen;

$R_2$ is hydrogen or an alkyl of 1 to 6 carbons;

$R_3$ is alkyl of 1 to 6 carbons, $-OH$ or $-O-$alkyl of 1 to 6 carbon atoms; $R_4$ an alkyl of 2 to 10 carbons or alkenyl of 3 to 10 carbons;

$R_5$ is hydrogen or $-CO_2H$;

$R_6$ is ortho-tetrazolyl or $-CO_2H$; and

X is $-N-$ or

where $R_5'$ is hydrogen or $-CO_2H$.

3. A compound of claim 1 wherein $R_1$ is chlorine;

$R_2$ is ethyl or hydrogen;

$R_3$ is $-OH$;

$R_4$ is n-butyl;

$R_5$ is hydrogen;

$R_6$ is ortho-tetrazolyl;

X is

$R_5'$ is hydrogen; and the imidazole nucleus is bonded to the 4-position of the indole.

4. The compound as recited in claim 1, [2-Butyl-1-[[1-(2H-tetrazol-5-yl)phenyl]-1H-indol-4-yl]-methyl]-1H-imidazol-4-yl]phosphonic acid, monoethyl ester, or a pharmaceutically acceptable salt or prodrug thereof.

5. The compound as recited in claim 1, [4-Bromo-2-butyl-1-[[1-[2-(2H-tetrazol-5-yl)phenyl]-1H-indol-4-yl]methyl]-1H-imidazol-5-yl]phosphonic acid, monoethyl ester, or a pharmaceutically acceptable salt or prodrug thereof.

6. The compound as recited in claim 1, [4-Bromo-2-butyl-1-[[1-[2-(2H-tetrazol-5-yl)phenyl]-1H-indol-4-yl]methyl]-1H-imidazol-5-yl]phosphonic acid, or a pharmaceutically acceptable salt or prodrug thereof.

7. The compound as recited in claim 1, [2-Butyl-4-chloro-1-[[1-[2-(2H-tetrazol-5-yl)phenyl]-1H-imidazol-5-yl]phosphonic acid, monoethyl ester, or a pharmaceutically acceptable salt or prodrug thereof.

8. The compound as recited in claim 1, [2-Butyl-4-chloro-1-[[1-[2-(2H-tetrazol-5-yl)phenyl]-1H-indol-4-yl]methyl]-1H-imidazol-5-yl]phosphonic acid, monomethyl ester, or a pharmaceutically acceptable salt or prodrug thereof.

9. The compound as recited in claim 1, [2-Butyl-4-chloro-1-[[1-[2-(2H-tetrazol-5-yl)phenyl]-1H-indol-4-yl]methyl]-1H-imidazol-5-yl]phosphonic acid, or a pharmaceutically acceptable salt or prodrug thereof.

10. The compound as recited in claim 1, [4-chloro-2-propyl-1-[[1-[2-(2H-tetrazol-5-yl)phenyl]-1H-indol-4-yl]methyl]-1H-imidazol-5-yl]phosphonic acid, or a pharmaceutically acceptable salt or prodrug thereof.

11. The compound as recited in claim 1, [2-Butyl-4-chloro-1-[[1-[2-(2H-tetrazol-5-yl)phenyl]-1H-indol-4-yl]methyl]-1H-imidazol-5-yl]phosphonic acid, diethyl ester, or a pharmaceutically acceptable salt or prodrug thereof.

12. The compound as recited in claim 1, [2-Butyl-1-[[1-[2-(2H-tetrazol-5-yl)phenyl]-1H-indol-4-yl]methyl]-1H-imidazol-5-yl]phosphonic acid, monoethyl ester, or a pharmaceutically acceptable salt or prodrug thereof.

13. The compound as recited in claim 1, [4—Chloro-2-propyl-1-[[1-[2-(2H-tetrazol-5-yl)phenyl]-1H-indol-4-yl]methyl]-1H-imidazol-5-yl]phosphonic acid, monoethyl ester, or a pharmaceutically acceptable salt or prodrug thereof.

14. The compound as recited in claim 1, [2-Butyl-4-bromo-1-[[1-[2-(2H-tetrazol-5-yl)phenyl]-1H-indol-4-yl]methyl]-1H-imidazol-5-yl]methylphosphonic acid, or a pharmaceutically acceptable salt or prodrug thereof.

15. The compound as recited in claim 1, [2-Butyl-4-chloro-1-[[1-[2-(2H-tetrazol-5-yl)-phenyl]-1H-indol-4-yl]methyl]-1H-imidazol-5-yl]methylphosphinic acid, or a pharmaceutically acceptable salt or prodrug thereof.

16. A pharmaceutical composition comprising a compound of claim 1 and a pharmaceutically acceptable carrier.

17. A method for treating hypertension comprising administering to a mammalian specie in need thereof a therapeutically effective amount of a composition of claim 16.

18. A method for treating congestive heart failure comprising administering to a mammalian specie in need thereof a therapeutically effective amount of a composition of claim 16.

19. A method for preventing cardiac hypertrophy comprising administering to a mammalian specie in need thereof a therapeutically effective amount of a composition of claim 16.

* * * * *

UNITED STATES PATENT AND TRADEMARK OFFICE
CERTIFICATE OF CORRECTION

PATENT NO. : 5,208,235
DATED : May 4, 1993
INVENTOR(S) : Michael A. Poss

It is certified that error appears in the above-identified patent and that said Letters Patent is hereby corrected as shown below:

The structure of the compound of formula I in the:

1) Abstract;
2) Summary of the Invention, Column 1, lines 15 to 30; and
3) Claims, Column 29, lines 15 to 29 should be as follows:

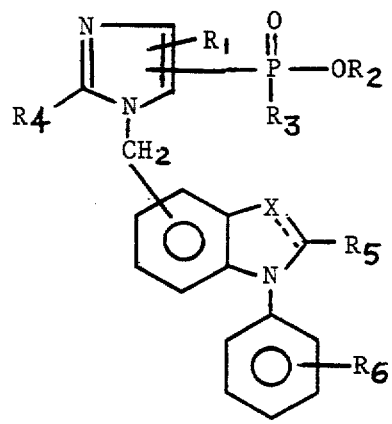

Signed and Sealed this

Sixteenth Day of August, 1994

Attest:

BRUCE LEHMAN

Attesting Officer

Commissioner of Patents and Trademarks